United States Patent [19]

Woodroof et al.

[11] Patent Number: 4,502,159
[45] Date of Patent: Mar. 5, 1985

[54] TUBULAR PROSTHESES PREPARED FROM PERICARDIAL TISSUE

[75] Inventors: E. Aubrey Woodroof, Fountain Valley; Philip S. Yang, Irvine, both of Calif.

[73] Assignee: Shiley Incorporated, Irvine, Calif.

[21] Appl. No.: 407,529

[22] Filed: Aug. 12, 1982

[51] Int. Cl.³ .............................................. A61F 1/00
[52] U.S. Cl. .............................................. 3/1.4; 3/1; 128/1 R
[58] Field of Search ................. 3/1, 1.4, 1.5; 112/441, 112/269.1

[56] References Cited

U.S. PATENT DOCUMENTS

| | | | |
|---|---|---|---|
| 2,978,787 | 4/1961 | Liebig | 3/1.4 |
| 3,142,067 | 7/1964 | Liebig | 3/1.4 |
| 4,209,859 | 7/1980 | Hoffman | 3/1.4 |
| 4,222,377 | 9/1980 | Burton | 128/DIG. 25 |

OTHER PUBLICATIONS

Sako, "Prevent. of Dilation in Autogenous Venous and Pericardial Grafts in the Thoracic Aorta", Surgery, 30, pp. 148–160 (1951).
Allen R. et al., "Modified Blalock Shunts Utilizing Pericardial Tube Grafts", Jour. Pediatr. Surg., 12(3), pp. 287–294 (1977).
Zapolanski A. et al., "Pericardial Graft for Intraoperative Balloon Pump Insertion", Ann. Thoracic Surg., 33(5), pp. 516–517 (May 1982).
Ornvold K. et al., "Structural Changes of Stabilized Porcine Pericardium After Experimental and Clinical Implantation", in Proc. Eur. Soc. for Artif. Organs, vol. VI, pp. 248–257, Geneva, Switzerland (1979).
"Polystan Bioprostheses", Polystan A/S, Copenhagen, Denmark, Oct. 1979 Brochure.

Primary Examiner—Richard J. Apley
Assistant Examiner—David Isabella
Attorney, Agent, or Firm—Charles J. Knuth; Peter C. Richardson; Lawrence C. Akers

[57] ABSTRACT

Novel tubular prostheses, e.g. vascular or ureteral prostheses, prepared by sewing the opposed edges of a sheet of pericardial tissue together with a thread to form a longitudinal seam are disclosed. By disposing the thread in a suitable configuration along the seam, for example in a plurality of stitches each of which is secured with a knot, a tubular prosthesis results that can be cut transversely between its ends without unravelling the thread and substantially damaging the same. Use of bovine pericardial tissue is preferred since the range of compliances of tubular prostheses made therefrom is approximately comparable to the range in human arteries and veins, whereas tubular prostheses made from porcine pericardial tissue tend to be too compliant.

4 Claims, 19 Drawing Figures

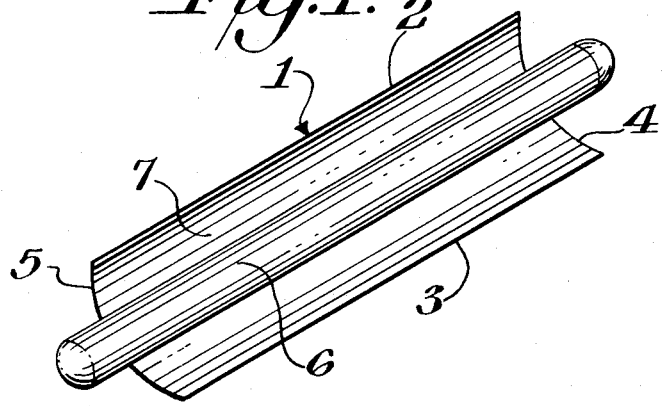
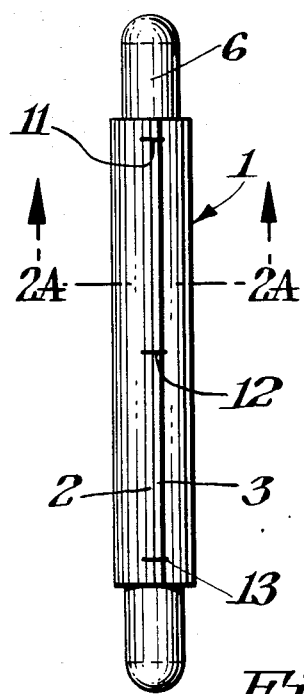
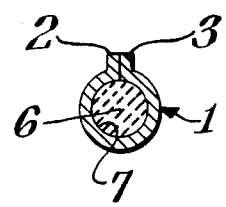
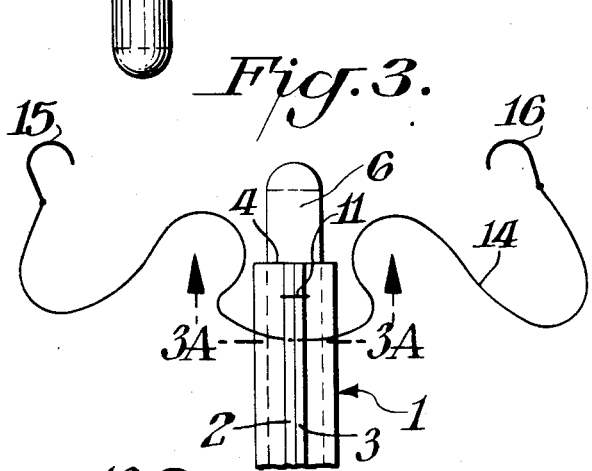
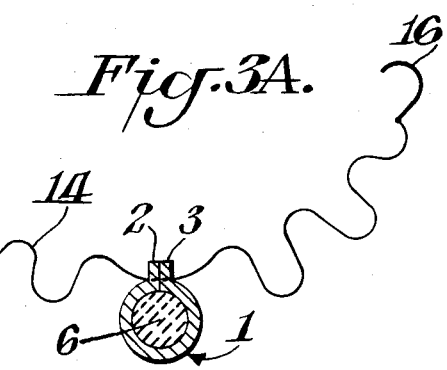
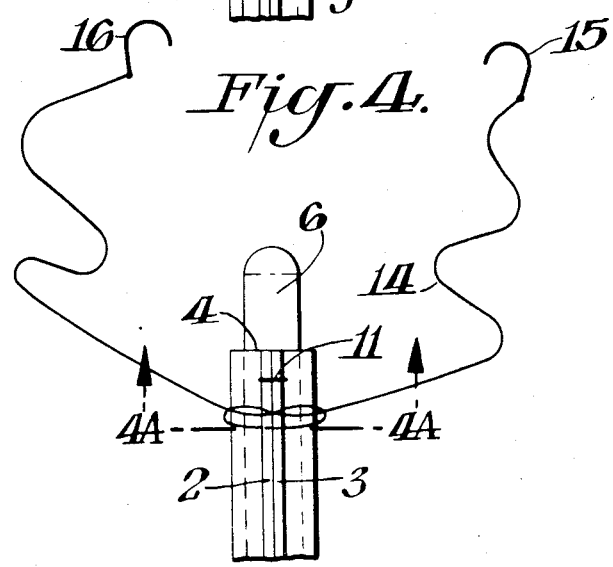
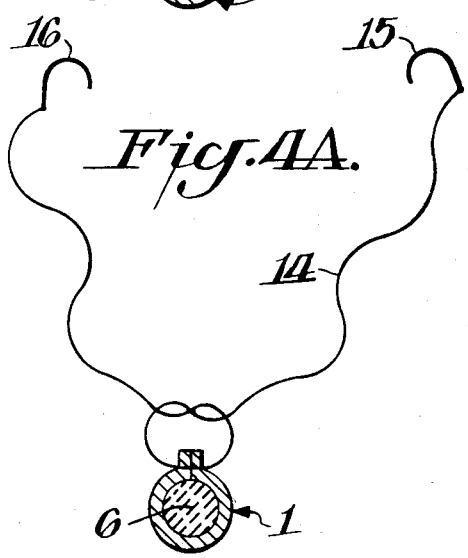

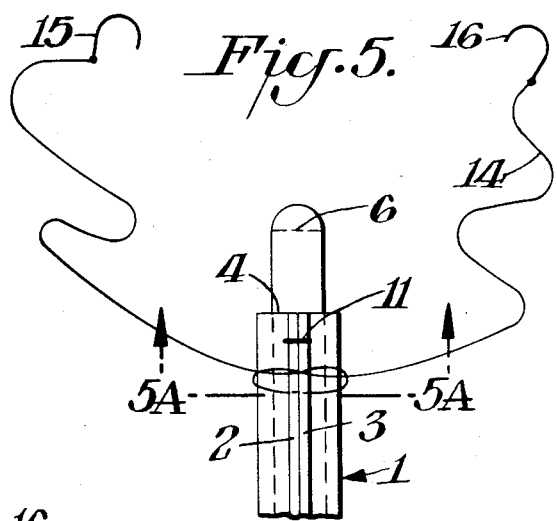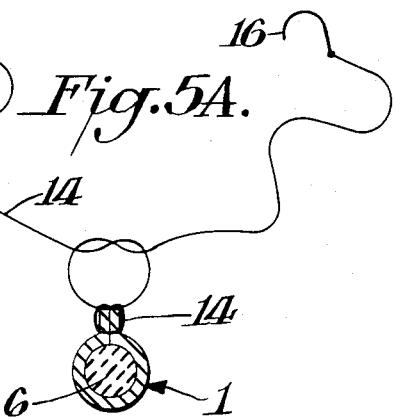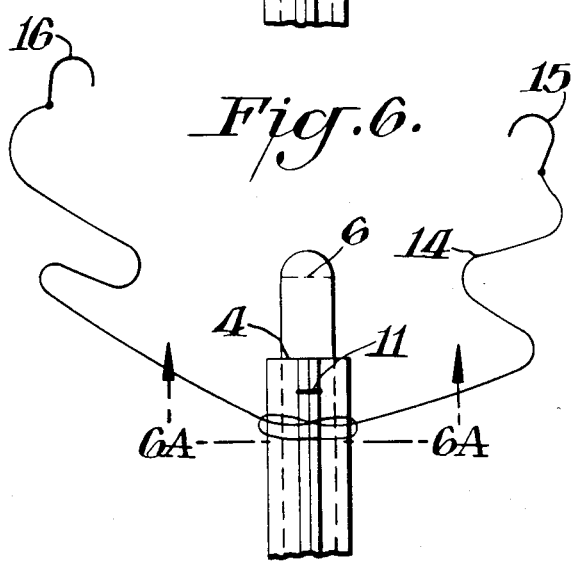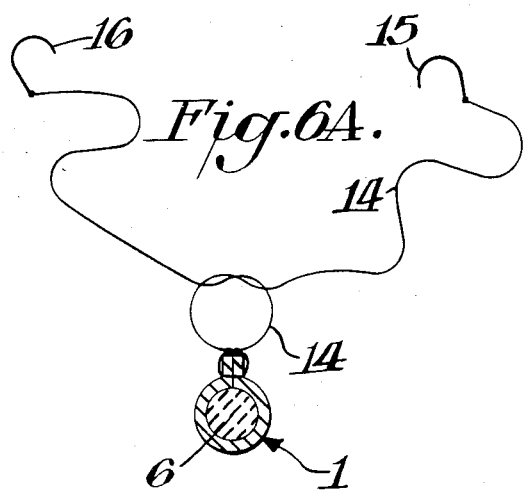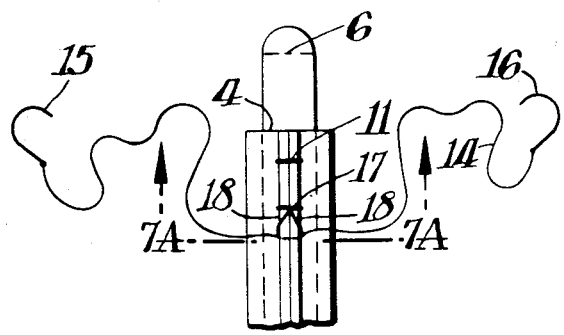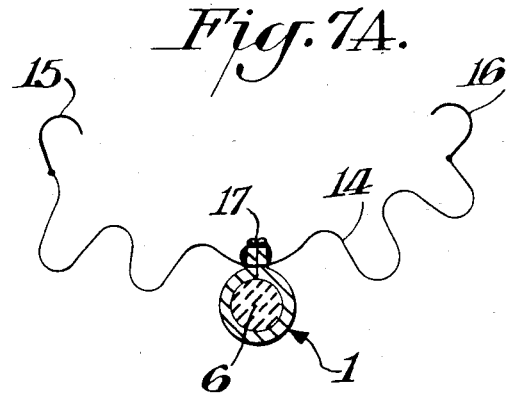

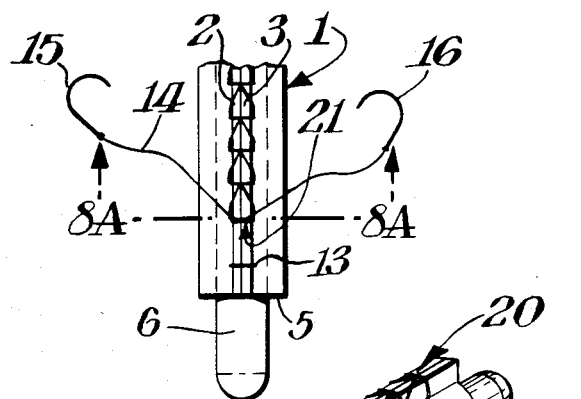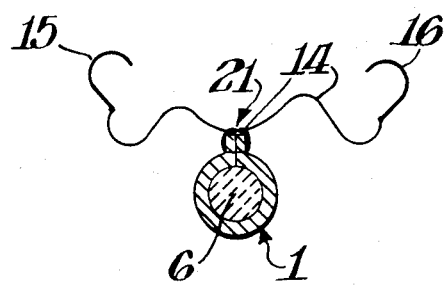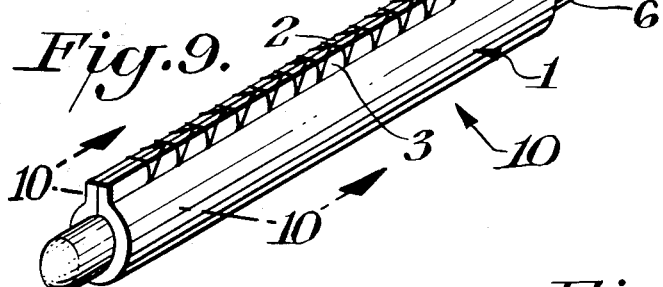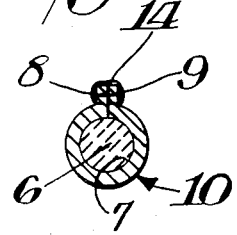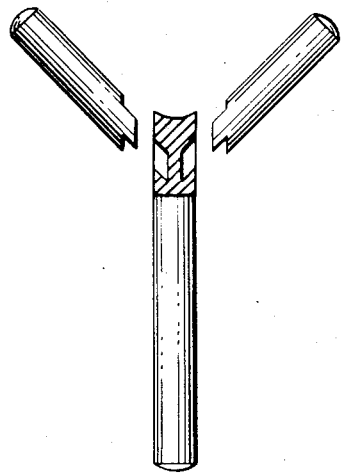

TUBULAR PROSTHESES PREPARED FROM PERICARDIAL TISSUE

BACKGROUND OF THE INVENTION

Tubular prostheses made from natural tissue have been widely used in recent years in the surgical repair and replacement of diseased or damaged blood vessels in human patients. Natural tissue prostheses fall into three general classes. Autogenous material tissue prostheses are prepared from tissues taken from the patient's own body (e.g., saphenous vein grafts). Use of such prostheses eliminates the possibility of rejection of the implanted prosthesis, but requires a more extensive and time-consuming surgical intervention with attendant risks to the patient. Homologous natural tissue prostheses are prepared from tissue taken from another human, while heterologous natural tissue prostheses are prepared from tissue taken from another species. The use of homologous and heterologous umblical cord vessels as, e.g., vascular and ureteral prostheses is disclosed in U.S. Pat. Nos. 3,894,530; 3,974,526 and 3,988,782.

Autogenous vascular prostheses prepared from sheets of pericardial tissue have been disclosed by Yoshio Sako, "Prevention of Dilation in Autogenous Venous and Pericardial Grafts in the Thoracic Aorta", *Surgery*, 30, pp. 148–160 (1951) and by Robert G. Allen and Francis H. Cole, Jr., "Modified Blalock Shunts Utilizing Pericardial Tube Grafts", *Jour. Pediatr. Surg.*, 12(3), pp. 287–294 (1977). Heterologous vascular prostheses prepared from sheets of porcine pericardial tissue have been disclosed by Ornvold K. et al., "Structural Changes of Stabilized Porcine Pericardium after Experimental and Clinical Implantation", in *Proc. Eur. Soc. for Artif. Organs*, Vol. VI, Geneva, Switzerland (1979).

The necessary characteristics of a tubular vascular prosthesis are biological compatibility, adequate strength, resistance to infection, resistance to biological degradation, non-thrombogenicity and lack of a tendency to promote aneurysm formation. As used in this application the term biological compatibility means that the prosthesis is non-toxic in the in vivo environment of its intended use, and is not rejected by the patient's physiological system (i.e. is non-antigenic). Furthermore, it is desirable that the prosthesis be capable of production at an economical cost in a wide variety of lengths, diameters and shapes (e.g., straight, curved, bifurcated), be readily anastomosed to the patient's body and to other tubular prostheses of the same or different type, exhibit dimensional stability in use, and, in order to minimize hemodynamic turbulence and trama to the native vessel, have a compliance comparable to that of the patient's natural vessel that it is repairing or replacing (see discussion of compliance in U.S. Pat. No. 4,173,689). Finally, it is disadvantageous because of the risk of kinking to implant a tubular prosthesis that is too long for the intended application. On the other hand, implantation of a prosthesis that is too short places excessive tension on the anastomoses at its ends, thereby resulting in trama to said anastomoses. Thus, it would be highly desirable to provide a tubular prosthesis that can be cut transversely to a desired length at any point between its ends without otherwise substantially damaging the prosthesis.

SUMMARY OF THE INVENTION

A novel tubular prosthesis has now been invented which comprises a sheet of pericardial tissue having opposed edges sewn together by means including a thread to form a longitudinal seam, with the thread being disposed in a configuration including a plurality of stitches extending along the seam, wherein the configuration of the thread is such that the prosthesis can be cut transversely between its ends, thereby severing the thread, without substantial damage to the seam (e.g., without causing the thread to unravel). Thus, for example, each of said stitches may be secured with a knot tied in the thread after the stitch. Preferably, in order to reduce the possibility of thrombus formation, the opposed edges of the sheet of pericardial tissue are sewn together to form an everted seam, and the smooth mesothelial side of the tissue is disposed luminally.

The novel prosthesis of the invention may be of either the autogenous, homologous or heterologous type, with the latter preferred. Additionally, the tubular prosthesis of the present invention preferably comprises a sheet of bovine pericardial tissue having opposed edges sewn together to form a longitudinal seam. The range of compliances of bovine pericardial tissue tubular prostheses is approximately comparable to the range in human arteries and veins, while porcine pericardial tissue tubular prostheses tend to be too compliant.

DETAILED DESCRIPTION OF THE INVENTION

The invention will be described in detail with reference to a preferred embodiment thereof, which is a tubular vascular prosthesis prepared from bovine pericardial tissue. Reference to this embodiment does not limit the scope of the invention, which is limited only by the scope of the claims. In the drawings:

FIGS. 1 to 8 illustrate several steps in the manufacture of a tubular vascular prosthesis 10 of the invention from a sheet of bovine pericardial tissue;

FIGS. 2A to 8A are transverse cross-sectional views of the prosthesis at the various steps in the manufacture thereof illustrated in FIGS. 2 to 8;

FIG. 9 is a perspective view of the finished tubular prosthesis 10;

FIG. 10 is an end elevation view of the finished tubular prosthesis 10;

FIG. 11 is an exploded front elevation view of a bifurcated mandrel for use in preparing a bifurcated tubular prosthesis of the invention; and FIG. 12 is a front elevation view of a longitudinally tapered mandrel for use in preparing a longitudinally tapered prosthesis of the invention.

The starting material in the manufacture of a tubular vascular prosthesis 10 of the invention is a roughly cut strip of bovine pericardial tissue. After excision, the strip is cleaned of fat, fibers and extraneous debris and may then be placed in phosphate buffered saline solution for temporary storage. Subsequently, the strip is neatly trimmed into the shape of a rectangular sheet 1 having opposed long edges 2 and 3 slightly longer than the desired length of the prosthesis. The length of opposed short edges 4 and 5 of rectangular sheet 1 is determined by the desired inner diameter of prosthesis 10; for example, when the desired inner diameter is 4 mm., short edges 4 and 5 are at least 1.5 cm. long.

As shown in FIG. 1, unfixed sheet 1 is wrapped around a cylindrical glass rod 6, with the smooth mesothelial side 7 of the sheet facing the rod. Edges 2 and 3 are temporarily held together during the sewing operation in an everted seam (see FIGS. 2 and 2A) by means of three evenly spaced single temporary sutures 11, 12 and 13 tied in square knots. Glass rod 6 serves as a mandrel and thus has a diameter of 4 mm., the desired inner diameter of prosthesis 10. By using rods having different diameters, the diameter of the resulting cylindrical prosthesis may be infinitely varied. Additionally, the mandrel (and hence the resulting prosthesis) may be, e.g., bifurcated or tapered with decreasing cross-sectional area longitudinally (see FIGS. 11 and 12). The mandrel may have non-circular cross-sections in transverse planes, but a circular cross-section is usually preferred.

After sutures 11, 12 and 13 have been tied, opposed edges 2 and 3 are permanently sewn together with a suture 14 to form an everted longitudinal seam 20. Suture 14 is provided with suture needles 15 and 16 at its ends and is thus of the double-armed type. Preferably, it is a double-armed C-1, 6-0 monofilament polypropylene suture (Ethicon, Inc.; Somerville, N.J.). Edges 2 and 3 are permanently sewn together in such a manner that suture 14 is disposed in a configuration including a plurality of stitches extending along seam 20, with each of the stitches being secured with a knot tied in suture 14 after the stitch. One technique for creating such a configuration is illustrated in FIGS. 3 to 8 and 3A to 8A. At the top of the seam, about 3 mm. from edge 4 (see FIGS. 3 and 3A), one of the ends of suture 14 is passed through the two juxtaposed everted portions of sheet 1 and then interlaced with the other end of suture 14 in the familiar "left-over-right" pattern (or vice-versa) to form the first winding of a square knot (see FIGS. 4 and 4A). This first winding is then snugly tightened against the long edges of sheet 1 by pulling the ends of suture 14 apart. The ends of suture 14 are then interlaced (see FIGS. 5 and 5A) in a "right-over-left" pattern (or "left-over-right" if the first winding was "right-over-left) to form a square knot, which is then snugly tightened. Finally, the ends of suture 14 are interlaced one more time in a "left-over-right" pattern (or "right-over-left") and then pulled apart to yield a securely tied triple knot 17 at the top of the seam (see FIGS. 6 and 6A). The two ends of suture 14 are then both passed through the two juxtaposed everted portions of sheet 1 at a location about 2 mm. below (i.e. displaced in a longitudinal direction from) triple knot 17 and pulled to form tightened stitch 18, the first stitch in the configuration (see FIGS. 7 and 7A). Stitch 18 is then secured with a triple knot tied in the manner described above with reference to knot 17. This sequence of stitch and knot, with each knot displaced longitudinally from the preceding one by about 2 mm., is continuously repeated (suture 12 is removed when the seamstress reaches it) until a final triple knot 21 is tied about 3 mm. from edge 5 (see FIGS. 8 and 8A) and the exposed ends of suture 14 cut. Sutures 11 and 13 are then removed and the short edges 4 and 5 of sheet 1 trimmed just short of knots 17 and 21, respectively. As can be seen in FIGS. 9 and 10, opposed long edges 2 and 3 of sheet 1 have been sewn together to form everted longitudinal seam 20, with longitudinal strips 8 and 9 of the surface of the mesothelial side 7 facing one another along the seam. Prosthesis 10 is adapted to be readily anastomosed to another like or different prosthesis or to the natural tissue in the patient's body. If desired, several prostheses such as prosthesis 10 may be anastomosed together end-to-end.

As shown in FIGS. 9 and 10, prosthesis 10 is manufactured such that the smooth mesothelial side 7 of sheet 1 is disposed luminally and such that longitudinal seam 20 is everted. These dispositions are preferred in order to reduce surface irregularities on the inner wall of the prosthesis and thus minimize the risk of thrombus formation.

The configuration of stitches and securing knots illustrated in FIGS. 3 to 8 and 3A to 8A is adapted to be sewn by hand. Other configurations of stitches and securing knots may of course be employed. In the broadest conception of this aspect of the invention, the thread used to sew the opposed edges of the sheet of percardial tissue together to form a longitudinal seam is disposed in a configuration including a plurality of stitches extending along said seam, with said configuration being any such that the resulting tubular prosthesis can be cut transversely between its ends without substantially damaging the seam. Thus, the opposed edges of the sheet of pericardial tissue may be sewn together with a sewing machine, for example in a double overlock stitch. One commercially available sewing machine that may be used to obtain a double overlock stitch is an Elna Model 68SU (Tavaro S.A., Geneva, Switzerland; Disc. No. 163, Stitch Selector-7, Stitch Length Dial-S, Stitch Width Selector-O or other than O). Since the tubular prosthesis can be cut transversely between its ends without substantially damaging the seam, its length can be adjusted as necessary to adapt to a particular surgical situation. Thus the risks associated with having to implant a prosthesis longer or shorter than desired are eliminated.

It is highly preferred that the pericardial tissue be fixed with a cross-linking agent while it is on the mandrel, after the sewing operation has been completed. The purpose of the cross-linking agent treatment is to increase the strength and resistance to biological degradation of the prosthesis, and to insure that the prosthesis retains its desired dimensions in vivo after implantation. Thus, on the latter point, if the sheet of pericardial tissue is fixed as a flat sheet before it is wrapped and sewn around the mandrel, it will have a tendency to try to return to the flat configuration. As a result, the cross-section of the lumen of the implanted prosthesis will tend to deform into a pear-like shape, with the seam at the V-shaped tip of the pear, and the possibility of thrombus formation will be increased. If, on the other hand, the mandrel were removed (and not replaced) before fixation, the desired prosthesis dimensions would have to be maintained during the fixation step by another means, e.g., internal pressurization of the prosthesis (see, e.g., U.S. Pat. No. 4,050,893).

The sheet of pericardial tissue is fixed while on the mandrel by contacting the sewn prosthesis with an aqueous solution of a cross-linking agent for the pericardial tissue, e.g. by placing the prosthesis and mandrel for at least seven days at room temperature in a bath containing a 0.5 wt. percent aqueous solution of glutaraldehyde. Before contacting the prosthesis with cross-linking agent, entrapped air bubbles are removed from between the mandrel and the sheet of pericardial tissue, e.g. by removing the prosthesis and then slowly replacing it on the mandrel. If it is desired to produce a prosthesis that is curved in its longitudinal plane, i.e. that generally exhibits a C-shape when viewed externally, the prosthesis is first sewn upon a straight mandrel as illustrated in FIGS. 1 to 8 and then removed from that mandrel and placed upon a curved mandrel having the same diameter and the desired curvature, with the seam at the inside of the curve, for the cross-linking agent fixation step.

The sheet of pericardial tissue may also be treated with one or more antithrombogenic agents (e.g. heparin, albumin or a covalently bonded compound of heparin and albumin), fibrinolytic enzymes (e.g. urokinase) or antibiotics, which substances are then retained upon the surface of the sheet. Treatment of the sheet of pericardial tissue with heparin, albumin or a covalently bonded compound thereof is preferably carried out before the pericardial tissue fixation step, because the tissue cross-linking step serves not only to cross-link the tissue, but also to improve the retention of heparin, albumin and covalently bonded compounds thereof by cross-linking the e.g. heparin upon the surface of the prosthesis. Treatment with a fibrinolytic enzyme must take place after the pericardial tissue fixation step has been performed and residual cross-linking agent utilized in said step has been removed, e.g. by washing. The retention of fibrinolytic enzymes on the surface of the pericardial tissue may be improved by a treatment with a cross-linking agent, such as 1-ethyl(3,3-dimethylaminopropyl)carbodiimide hydrochloride, that reacts with free carboxyl groups on the surface of the pericardial tissue.

Most preferably, the sheet of pericardial tissue is treated with one or more of the above-indicated substances after it has been sewn into a tube on the mandrel. In the case of treatment with heparin, albumin or a covalently bonded compound thereof, the sewn tubular prosthesis is preferably removed from the mandrel so that its luminal surface is exposed, treated with e.g. heparin in an aqueous solution bath, and then slowly replaced upon the mandrel for the pericardial tissue fixation step. The tissue fixation step is conveniently performed by adding the tissue cross-linking agent to the same bath and replacing the tubular prosthesis therein. In the case of fibrinolytic enzyme treatment, the sewn and fixed tubular prosthesis is preferably removed from the mandrel and washed with aqueous saline solution to remove residual amounts of, e.g., glutaraldehyde, treated with a cross-linking agent that reacts with free carboxyl groups on the surface of the pericardial tissue, and then placed into an aqueous fibrinolytic enzyme solution bath.

The prosthesis may be tested for major leaks by closing its ends and pressurizing it with a saline filled syringe under hand pressure. Additionally, the tubular prosthesis may be encased in a tubular mesh of, for example, 32 gauge Dacron in order to further reduce the risk of aneurysm formation in vivo on the exterior surface of the prosthesis.

For sterilization purposes, the assembly of the tubular prosthesis and the mandrel, e.g. the glass rod, carrying it may be placed for at least 24 hours at room temperature in a tubular sterile glass container containing about 150 ml. of a filtered 4 wt. percent aqueous solution of formaldehyde. The prosthesis/mandrel assembly is then transferred to a second tubular sterile glass container containing about 150 ml. of a filtered 4 wt. percent aqueous solution of formaldehyde, and the glass container sealed with a screw top followed by a heat shrink seal. The prosthesis/mandrel assembly is supplied to users in this sealed glass container. Alternatively, the assembly of the tubular prosthesis and the mandrel carrying it may be sealed in a glass container in saline solution and sterilized with gamma radiation. Radiation sterilization must be utilized when the tubular prosthesis has been treated with a fibrinolytic enzyme.

In use, the sealed container is opened, the tubular prosthesis is pushed off the mandrel (in the case of a bifurcated prosthesis a mandrel is provided having at least one arm separable by unscrewing) and the tubular prosthesis is then thoroughly washed with a heparinized saline solution. After closing off the patient's body vessel that is to be repaired, replaced or augmented, a portion or the entirety of said vessel is surgically excised. The tubular prosthesis is anastomosed to the patient's body to re-establish a closed circuit and the repaired, replaced or augmented vessel is then re-opened. A cylindrical tubular prosthesis prepared from a sheet of bovine pericardial tissue and having a diameter of not more than about 4 mm. is particularly suited for use as a ureteral prosthesis.

We claim:

1. A tubular vascular prosthesis comprising a sheet of pericardial tissue having opposing longitudinal edges sewn together by means including a continuous biocompatible thread to form an everted longitudinal seam along the length of said prosthesis, said thread being disposed in a configuration of stitches extending continuously along said seam and with each of said stitches being separately secured with a knot tied in said thread after said stitch so as to permit said prosthesis to be cut transversely to a determined length at any point between its ends without exposing unsecured free thread ends and thereby substantially damaging the seam.

2. A prosthesis of claim 1 wherein each of said stitches is secured with a triple knot tied in said thread after said stitch.

3. A prosthesis of claim 1 wherein the mesothelial side of said sheet of pericardial tissue is disposed luminally.

4. A prosthesis of claim 1 wherein said sheet of pericardial tissue is rectangular and said prosthesis is substantially cylindrical in shape.

* * * * *